United States Patent
Yodfat et al.

(10) Patent No.: US 7,875,004 B2
(45) Date of Patent: Jan. 25, 2011

(54) METHOD AND SYSTEM FOR DETECTING AN OCCLUSION IN A TUBE

(75) Inventors: Ofer Yodfat, Maccabim-Reut (IL); Gavriel Iddan, Haifa (IL); Gil Senesh, Haifa (IL)

(73) Assignee: Medingo Ltd., Yoqneam Illit (IL)

( * ) Notice: Subject to any disclaimer, the term of this patent is extended or adjusted under 35 U.S.C. 154(b) by 483 days.

(21) Appl. No.: 11/810,854

(22) Filed: Jun. 6, 2007

(65) Prior Publication Data

US 2008/0021395 A1    Jan. 24, 2008

Related U.S. Application Data

(60) Provisional application No. 60/812,549, filed on Jun. 8, 2006.

(51) Int. Cl.
*A61M 1/00* (2006.01)
(52) U.S. Cl. ........................ 604/151; 604/153
(58) Field of Classification Search .......... 604/131, 604/151, 890.1
See application file for complete search history.

(56) References Cited

U.S. PATENT DOCUMENTS

| | | | |
|---|---|---|---|
| 4,369,780 A | | 1/1983 | Sakai ................ 128/214 E |
| 4,373,525 A | * | 2/1983 | Kobayashi ................ 417/63 |
| 4,690,673 A | * | 9/1987 | Bloomquist ............... 604/67 |
| 4,762,518 A | * | 8/1988 | Kreinick ................. 604/245 |
| 4,838,860 A | * | 6/1989 | Groshong et al. ......... 604/152 |
| 5,320,503 A | * | 6/1994 | Davis .................... 417/474 |
| 5,575,310 A | * | 11/1996 | Kamen et al. ......... 137/614.11 |
| 5,720,721 A | * | 2/1998 | Dumas et al. ............. 604/67 |
| 6,149,394 A | | 11/2000 | Allen ..................... 417/63 |
| 6,423,035 B1 | | 7/2002 | Das et al. ............... 604/155 |
| 6,458,102 B1 | * | 10/2002 | Mann et al. .............. 604/131 |
| 6,830,558 B2 | | 12/2004 | Flaherty et al. ........... 604/67 |
| 7,121,143 B2 | * | 10/2006 | Malmstrom et al. ........ 73/705 |
| 2002/0169439 A1 | * | 11/2002 | Flaherty ................ 604/891.1 |
| 2003/0167035 A1 | * | 9/2003 | Flaherty et al. ........... 604/67 |
| 2005/0178206 A1 | | 8/2005 | Malmstrom |
| 2006/0264835 A1 | * | 11/2006 | Nielsen et al. ........... 604/174 |
| 2007/0088267 A1 | * | 4/2007 | Shekalim ................ 604/134 |
| 2007/0106218 A1 | | 5/2007 | Yodfat et al. ............ 604/131 |
| 2008/0167641 A1 | * | 7/2008 | Hansen et al. ........... 604/891.1 |

FOREIGN PATENT DOCUMENTS

EP   1 818 664 A   8/2007
WO   WO 98/04301 A   2/1998

OTHER PUBLICATIONS

International Search Report, PCT No. PCT/IL2007/000684 dated Sep. 29, 2007.

* cited by examiner

*Primary Examiner*—Nicholas D Lucchesi
*Assistant Examiner*—Gerald Landry, II
(74) *Attorney, Agent, or Firm*—Mintz, Levin, Cohn, Ferris, Glovsky & Popeo P.C.

(57) ABSTRACT

Systems and methods for detecting an occlusion in a fluid delivery device are disclosed. The system includes a fluid delivery tube, an occlusion detection sensor configured to be coupled to the fluid delivery tube and further configured to detect occlusion within the fluid delivery tube. The fluid delivery tube includes an occlusion detection portion. The occlusion detection sensor is further configured to detect alteration of a shape of the occlusion detection portion when at least one condition occurs within the fluid delivery tube.

71 Claims, 12 Drawing Sheets

Fig. 5A
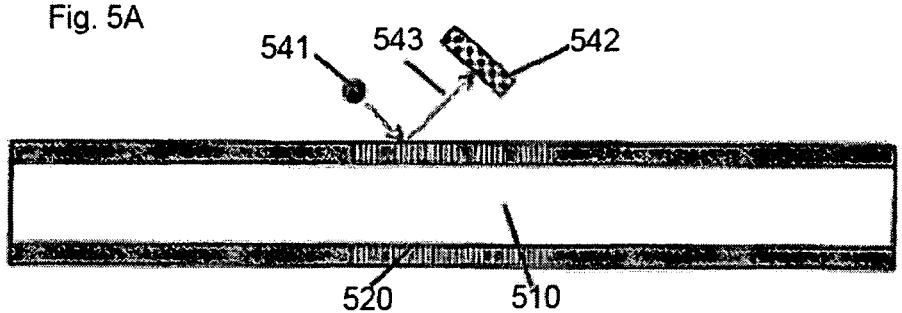
Fig. 5B
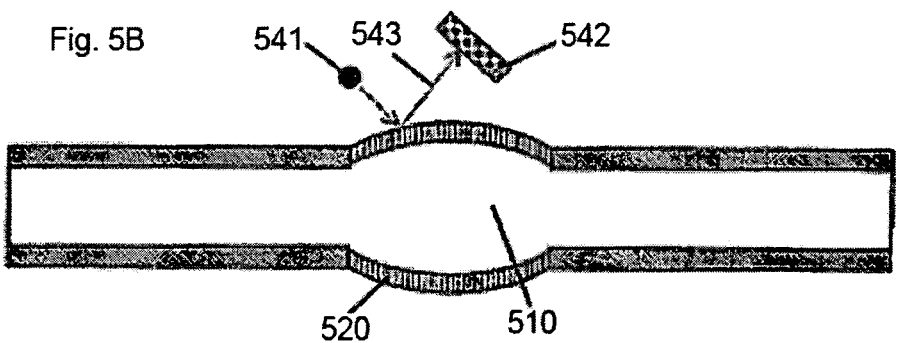
Fig. 5C
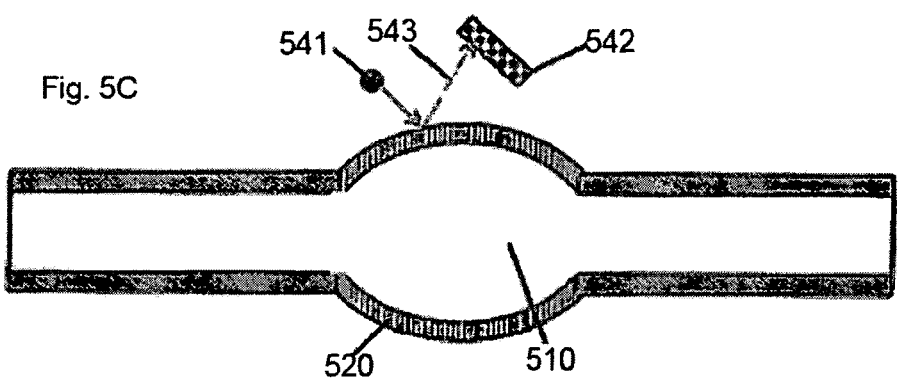
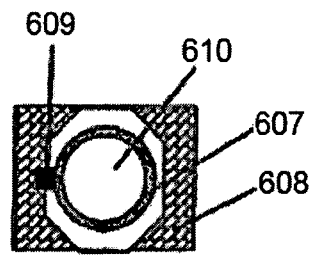
Fig. 6

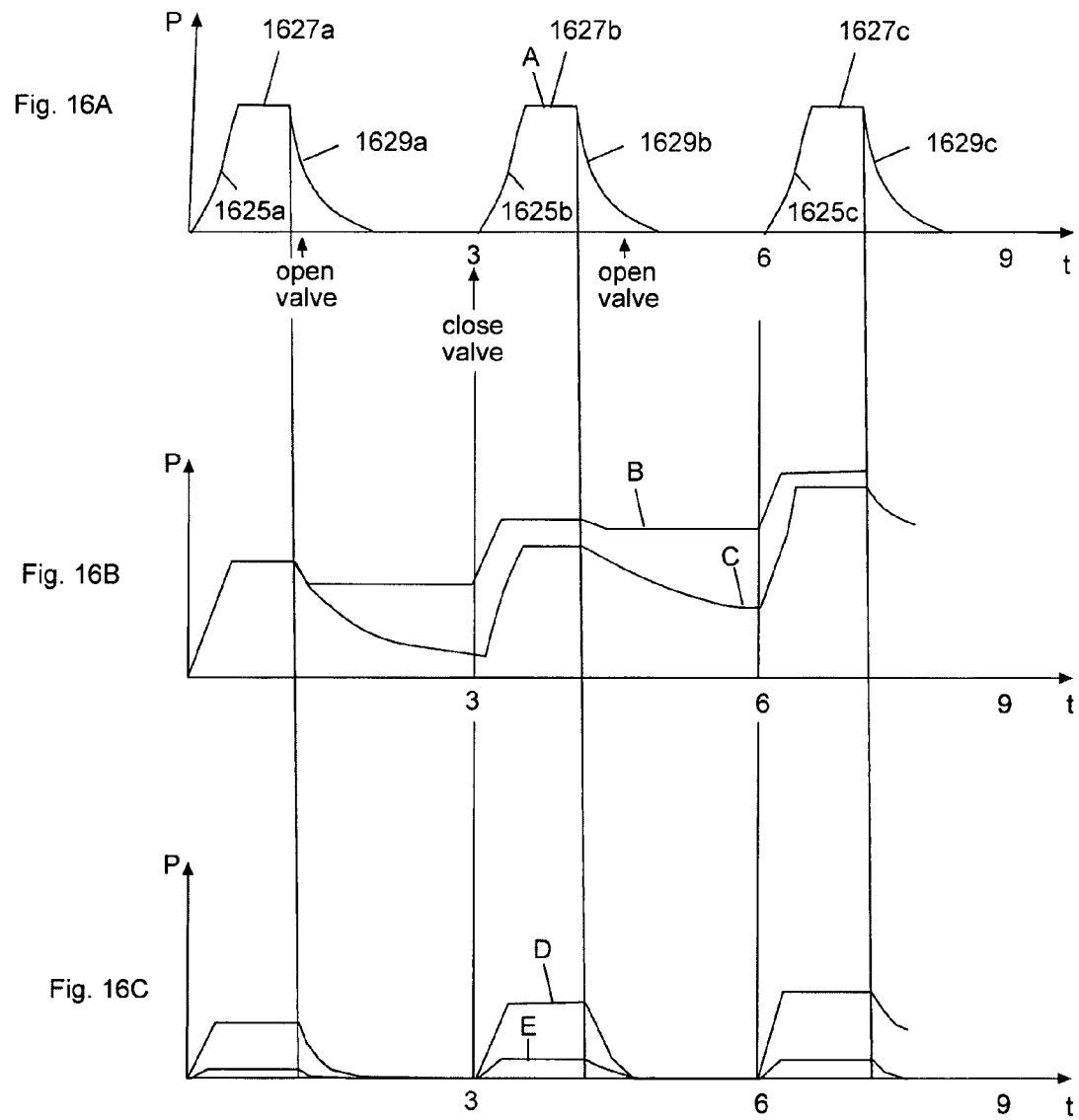

METHOD AND SYSTEM FOR DETECTING AN OCCLUSION IN A TUBE

CROSS-REFERENCE TO RELATED APPLICATION

The present application claims priority to U.S. Provisional Patent Application No. 60/812,549 to Yodfat, filed Jun. 8, 2006, and entitled "Method and System for Detecting an occlusion in a Tube." The present application also relates to Israel Patent Application No. 171813. The disclosures of the above applications are incorporated herein by reference in their entireties.

BACKGROUND OF THE INVENTION

1. Field of the invention

The present invention relates generally to a medical device for delivering fluids to a patient. Specifically, the invention relates to a small, low-cost, portable infusion device that can be used to transcutaneously deliver therapeutic fluids to a patient. The present invention also relates to systems and methods for detecting an occlusion in a fluid passageway in the infusion device that includes disposable and reusable parts.

2. Background

Conventional methods and systems for detecting an occlusion in a fluid delivery tube are based on a detection of tube's radial expansion. The expansion is caused by an elevation of an upstream pressure that is caused by a downstream occlusion. Exemplary conventional systems are disclosed in U.S. Pat. No. 4,373,525 to Kobayashi and U.S. Pat. No. 6,423,035 to Ras et al. Other conventional systems and methods for detecting an occlusion are disclosed in U.S. Pat. No. 4,369,780 to Sakai ("Sakai"), U.S. Pat. No. 6,149,394 to Allen ("Allen"), U.S. Pat. No. 6,830,558 to Flaherty et al. ("Flaherty").

Sakai discloses a magnet sensitive element for the detection of a flexible tube expansion. Allen discloses an apparatus and a method for detecting an occlusion using a portion of tube, which has a thinner wall section. When a downstream occlusion occurs, pressure elevation causes expansion of the thinner wall section of the tube. Flaherty discloses an apparatus and a method for detecting an occlusion by means of a sensor assembly that includes a resilient diaphragm having one surface positioned against the flow path's tube and a chamber wall positioned adjacent to the second surface of the diaphragm. A first electrode is positioned in the diaphragm, a second electrode is positioned in a fixed location and an impedance meter measures impedance between electrodes. In response to fluid flow conditions occurring in the flow path's tube, the second surface of the diaphragm expands and an electrical signal is provided accordingly.

However, most conventional systems and methods do not reliably detect an undesirable occlusion in the tube. The existing occlusion detectors are not sensitive enough and fail to detect partial occlusions. Further, most conventional detectors require a long lag time before alarming the patient of the occlusion. Additionally, they are expensive to produce and bulky.

Thus, there is a need for less expensive, accurate and sensitive systems and methods for the detection of partial and/or full occlusion(s) that may occur in the fluid infusion system.

SUMMARY OF THE INVENTION

The present invention relates to systems and methods for detecting an occlusion in a fluid passageway. An occlusion of a fluid passageway (e.g., a fluid delivery tube) is a common phenomenon, which can be caused by various reasons, e.g., aggregation of molecules of a therapeutic fluid, interference of a therapeutic fluid with tissue (for example, when the fluid is delivered by a subcutaneous insertion), tube kinking, cannula apposition etc. Occlusions occurring in an infusion device could be life threatening, and thus, there is a need to reliably detect occlusion at an early stage and alarm the patient before occurrence of any hazardous events associated with such occlusion.

In some embodiments of the present invention, detection and monitoring of occlusions within a passageway of a therapeutic fluid is especially advantageous in infusion devices or infusion pumps that can be configured to be attached to the body of a patient. Such attachment can be via adhesives and in this situation the fluid infusion device is designed as a dispensing patch unit. This dispensing patch unit or simply dispensing unit may have a reusable part and a disposable part. The reusable part includes components of a fluid metering system, electronic circuitry and other components (e.g., more expensive components of the system). The disposable part includes a downstream portion of the fluid delivery tube that can be configured to be monitored for occlusions and in which an occlusion is most likely to be detected.

In some embodiments, the present invention includes an infusion pump which propels therapeutic fluid through a flexible fluid delivery tube. The infusion pump can be configured to include an occlusion detection system. An occlusion causes an elevation of pressure and results in an expansion of the fluid delivery tube, which can be used for detecting the occlusion. In some embodiments, occlusions can be detected by measuring elevation of pressure or volume at discrete locations of fluid delivery tube.

In some embodiments, the present invention's occlusion detection is based on a downstream occlusion. The downstream occlusion causes elevation of upstream pressure within the fluid delivery tube. If the fluid delivery tube is short, pressure elevation is detectable immediately upon occlusion. In case of an elastic expandable tube, pressure elevation can be associated with an immediate radial expansion of tube which is also detectable.

In some embodiments of the invention, a short conducting tube is used for delivering a therapeutic fluid from a reservoir to the body of a patient. The tube can be made of a flexible material (e.g., silicone rubber, butyl rubber, polyurethane, etc.). During operation of the pump (whether continuous or not), a downstream occlusion can cause an increase in the fluid pressure and fluid volume in the tube.

In other embodiments of the invention, a portion of the tube can be deliberately weakened to allow immediate expansion and increase in diameter of the weakened tube portion. The weakening could be implemented by providing a portion of the delivery tube with a thinner wall or by using a stiffer tube on the remainder of the tube.

In some embodiments of the invention, an increase of the tube's diameter can be detected using an optical device or means. Such optical devices can be a combination of light detectors, and/or light collecting arrays that can be configured to detect light passing through the fluid delivery tube. As the light passes through the tube, the light detector device (e.g., CCD light collecting array) detects a change in light path as the light passes through the tube's expanded portion. In some embodiments, the light detector devices can include a light-collecting array and a light-emitting source, which can be positioned on the same or opposite sides of the tube's expanded portion.

In alternate embodiments of the invention, the expansion of the tube can be detected by the Bourdon effect. The Bourdon effect is a difference between the pressure inside a tube and the pressure outside the tube. If the inside pressure is greater than the outside pressure, the tube will expand. In these embodiments, the present invention can be configured to include an L-shape protrusion extending from the tube having a blind end. This change spatial configuration of the tube according to pressure elevations. In another embodiment, the light-emitting and collecting sources are positioned on the same side of the L-shape protrusion and optically sense conformation changes and corresponding pressure elevations.

In alternate embodiments of the present invention, occlusions can be electrically detected by a pressure sensor. Yet in other alternate embodiments, pressure elevation can be detected by a variation in capacitance. The system in the present invention can be configured to include a scissors-like assembly having one arm embracing the fluid delivery tube and a tail portion having one or more (preferably two) electrically conductive surfaces. A rise in pressure causes the tube diameter to change and, consequently, capacitance changes between the conductive surfaces. In some embodiments, capacitance measurement can be used for measuring quanta of the delivered therapeutic fluid (e.g., doses of basal and bolus insulin) as well as low pressure that is caused by fluid leakage.

In some embodiments, the present invention relates to a fluid delivery device for delivering therapeutic fluid to a patient. The system includes a fluid delivery tube and an occlusion detection sensor configured to be coupled to the fluid delivery tube and further configured to detect occlusion within the fluid delivery tube. The fluid delivery tube includes an occlusion detection portion. The occlusion detection sensor is further configured to detect alteration of a shape of the occlusion detection portion when at least one condition occurs within the fluid delivery tube.

In alternate embodiments, the present invention relates to a method of detecting an occlusion using a fluid delivery device for delivering therapeutic fluid to a patient. The fluid delivery device includes a fluid delivery tube having an occlusion detection portion and an occlusion detection sensor configured to be coupled to the fluid delivery tube. The method includes steps of delivering therapeutic fluid through the fluid delivery tube and detecting alternation of a shape of the occlusion detection portion of the fluid delivery tube when at least one condition occurs within the fluid delivery tube.

Further features and advantages of the invention, as well as structure and operation of various embodiments of the invention, are disclosed in detail below with references to the accompanying drawings.

BRIEF DESCRIPTION OF THE DRAWINGS

The present invention is described with reference to the accompanying drawings. In the drawings, like reference numbers indicate identical or functionally similar elements. Additionally, in most cases, the left-most digit(s) of a reference number identifies the drawing in which the reference number first appears.

FIGS. 5A-5C are longitudinal cross-sectional views of an exemplary tube with optical means for detecting an occlusion and having a light-collecting array and a light-emitting source positioned on the same side of the tube, according to the present invention.

FIG. 6 is a cross-sectional view of an exemplary tube having a pressure sensor configured to detect occlusion, according to the present invention.

FIGS. 16A-16C illustrate exemplary pressure-time graphs representing fluid delivery tube's pressure, where the tube includes a pulsating pumping mechanism and a valve, according to the present invention.

DETAILED DESCRIPTION OF THE INVENTION

Figure 1:
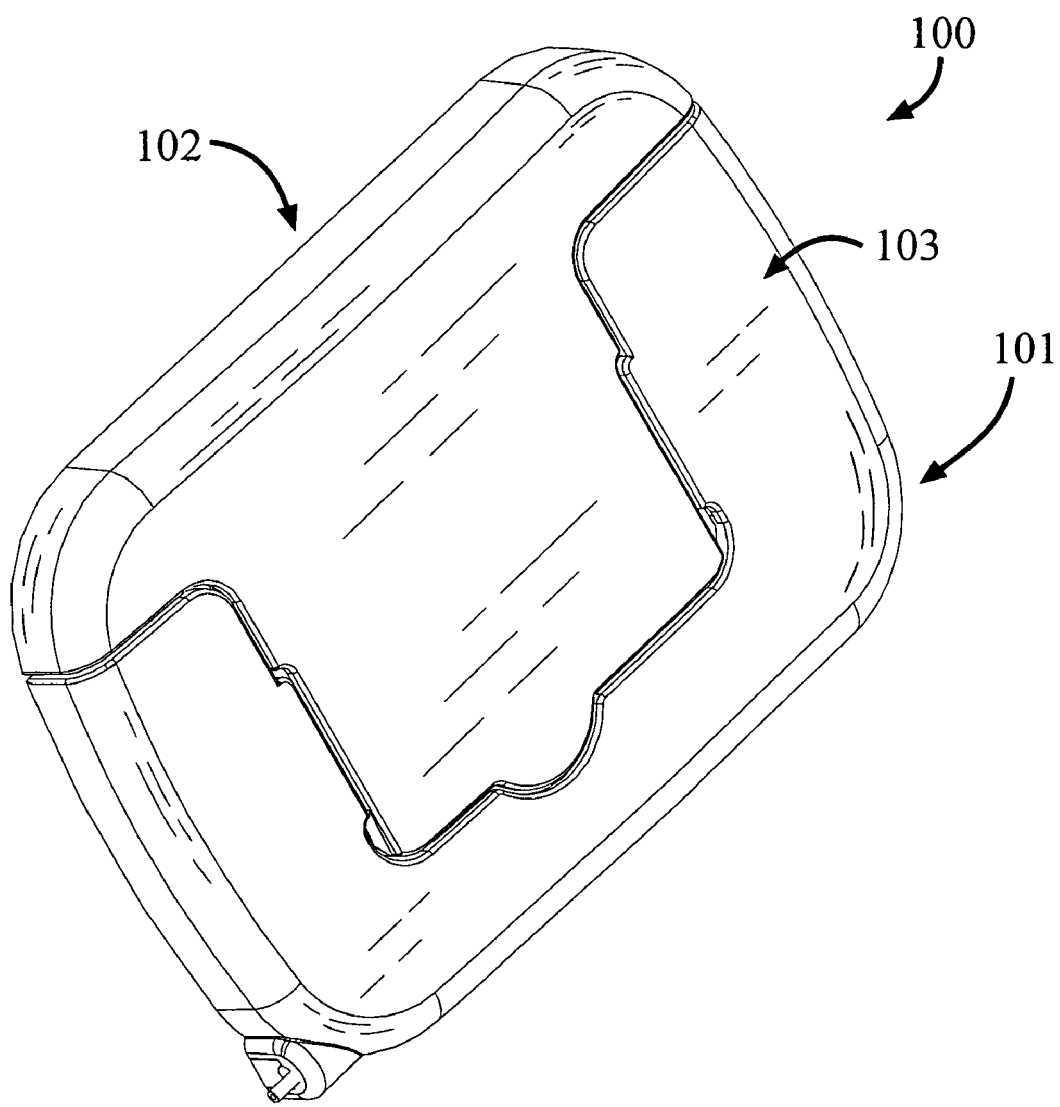
FIG. 1 illustrates an exemplary embodiment of a dispensing unit, according to the present invention.

FIG. 1 illustrates an embodiment of a fluid delivery device 100 having a dispensing unit 101, according to the present invention. In some embodiments of the invention, the fluid delivery device includes a dispensing unit configured to be adherable to the skin of the patient, and a separate remote control unit (not shown). In this situation the dispensing unit can be referred to as a dispensing patch unit. In the further description the term dispensing unit is equally applicable to an adherable to the skin (i.e. patch unit) and non-adherable to the skin dispensing units. The dispensing unit 101 is configured to include a disposable part 103 and a reusable part 102. This configuration of the fluid delivery device 100 is disclosed in Israel Patent Application No. 171813, disclosure of which is incorporated herein by reference in its entirety.

One of the advantages of this configuration is that the relatively expensive components of the dispensing unit 101 are contained within the reusable part 102 and less expensive components are contained within the disposable part 103. By virtue of this provision the use of the device 100 is more economical for the patient.

Figure 2A:
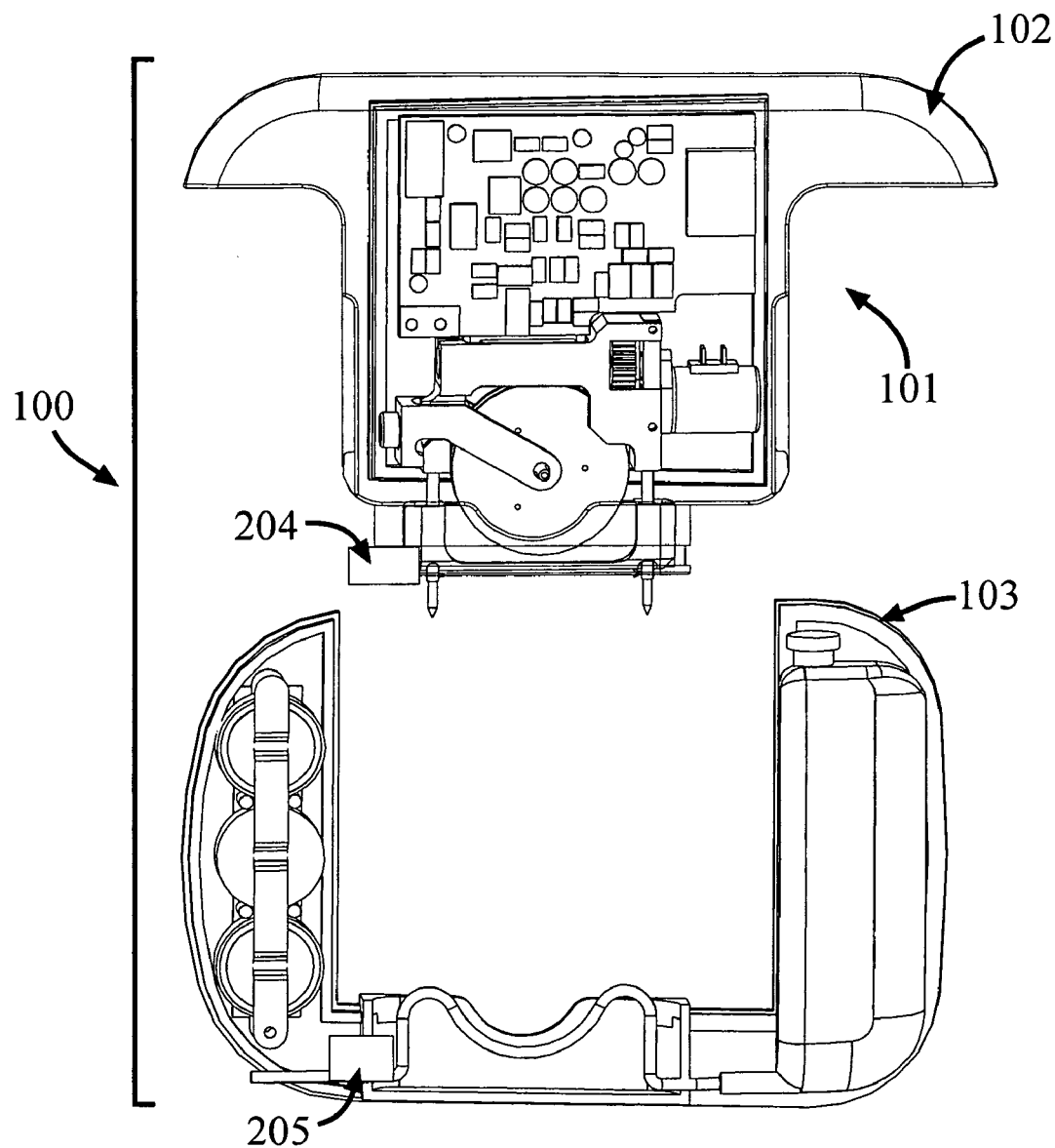
FIGS. 2A-2B illustrate exemplary embodiments of a disposable part and a reusable part of the dispensing unit, according to the present invention.

FIG. 2A illustrates the two parts of the dispensing unit 101. A reusable part 102 is configured to be operatively coupled to a disposable part 103. In some embodiments, the dispensing unit 101 can be configured to include an occlusion sensor, discussed below. The occlusion sensor can be a pressure sensor, a capacitance sensor, an optical sensor, or other type of sensor. In some embodiments, the occlusion sensor includes a reusable portion 204, and can be configured to include a disposable portion 205. The disposable portion 205 can be configured to be included in the reusable part 102 and/or disposable part 103 of the dispensing unit 101. Upon coupling the reusable part 102 and disposable part 103 (shown in FIG. 2B), the unit 101 including the occlusion sensor becomes operative. The unit 101 also includes a printed circuit board 214 ("PCB"). The PCB 214 includes a processor and other electronic components. Once the unit 101 becomes operative, the sensor is activated and configured to detect an occlusion in the fluid delivery tube. Also, the PCB 214 is configured to begin collecting data, processing, and performing data analysis.

Figure 2B:
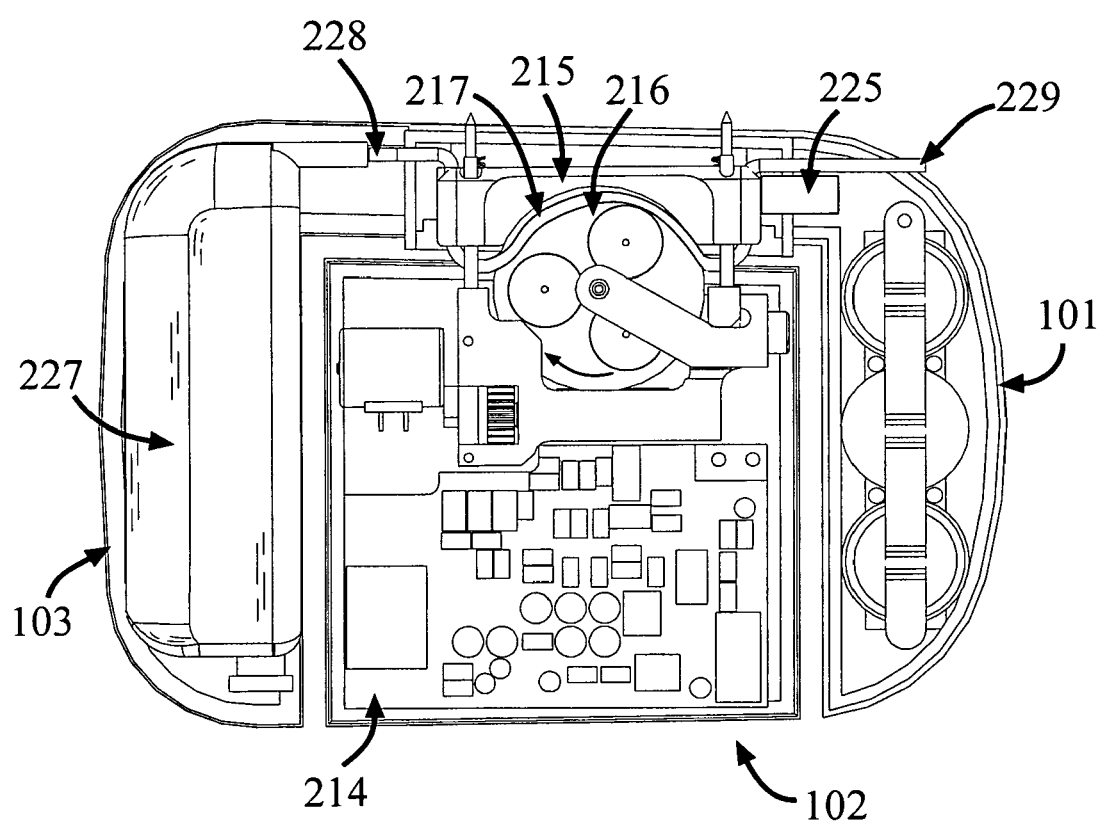
Figure 3A:
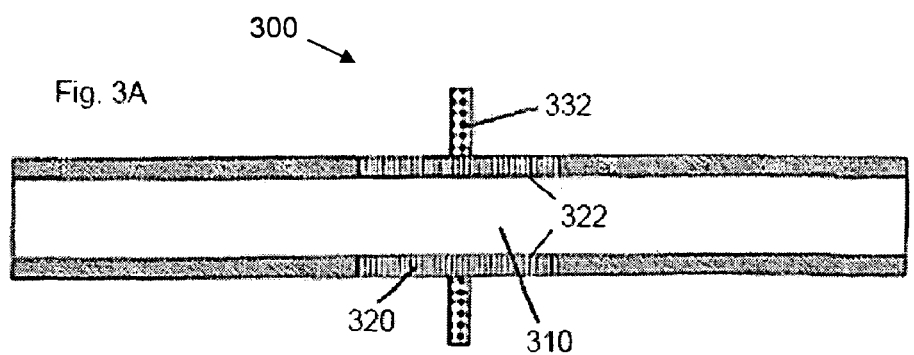
FIGS. 3A-3C are longitudinal cross-sectional views of an exemplary tube with optical means for detecting an occlusion and having a light-collecting array and a light-emitting source positioned on the opposite sides of the tube, according to the present invention.
Figure 3B:
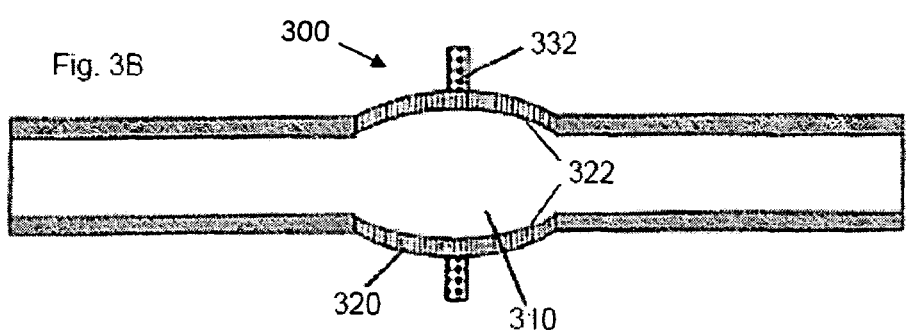
Figure 3C:
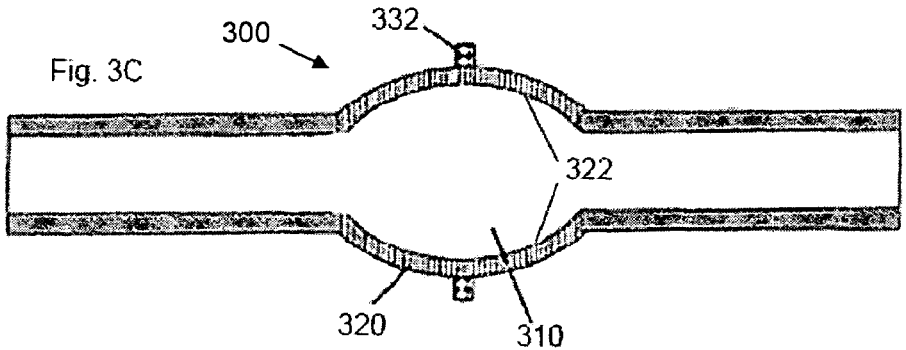
Figures 4A, 4B, 4C:
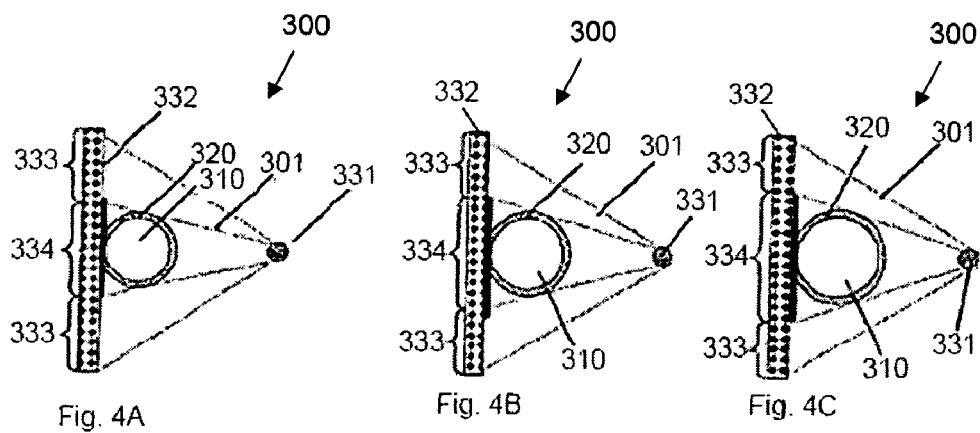
FIGS. 4A-4C are transverse cross-sectional views of an exemplary tube with optical means for detecting an occlusion and having a light-collecting array and a light-emitting source positioned on the opposite sides of the tube, according to the present invention.

FIG. 2B illustrates the reusable part 102 coupled to the disposable part 103. The disposable part 103 contains a reservoir 227. A delivery tube 217 connects an inlet portion 228 and an outlet portion 229. The inlet portion 228 is in flow communication with reservoir 227. The outlet portion 229 is connected to a subcutaneous cannula (not shown). The delivery tube 217 is placed between a stator plate 215 of the disposable part 103 and a peristaltic pump rotary wheel 216 within the reusable part 102.

Rotary wheel 216 rotates rollers that squeeze the delivery tube 217 against the stator plate 215. Thus, the therapeutic fluid is periodically pumped from the reservoir 227 via the inlet portion 228 to the delivery tube 217 and then via outlet portion 229 to the cannula (not shown). The device 100 further includes an occlusion sensor 225, which is configured to be placed near the outlet portion 229. The sensor 225 is configured to detect occlusion occurring downstream in the outlet portion 229 and/or in the cannula. In some embodiments, the dispensing unit 101 can include an alternative pumping mechanism, e.g., a syringe pump, piston pump, or any other pump suitable for these purposes.

FIGS. 3A-4C illustrate longitudinal and cross-sectional views of a delivery tube 310 configured with an optical device sensor for detecting an occlusion. The fluid delivery tube 310 includes a dedicated region 320. The dedicated region 320 is configured to be defined by sidewalls 322. The sidewalls 322 are configured to be manufactured from a more expendable elastic material than the rest of the tube. The optical device 300 further includes a light-collecting array 332 and a light-emitting source 331 (shown in FIGS. 4A-4C). The array 332 and the source 331 are configured to be positioned on opposite sides of the fluid delivery tube 310. The source 331 is configured to emit light 301 toward the array 332. Because emitted light 301 encounters the fluid delivery tube 310 on its path, the fluid delivery tube 310 casts a shadow on the array 332 (illustrated by the dark-colored or shaded zones 334 in FIGS. 4A-4C). The zones over which the delivery tube 310 does not cast a shadow are designated as light-colored zones 333 in FIGS. 4A-4C. When downstream occlusion occurs, it induces radial expansion of the dedicated region 320. This is illustrated in FIGS. 3B-3C and FIGS. 4B-4C. Because of such expansion, the shadow cast by the expanded region 320 is greater than the shadow cast by the unexpanded region 320, thus, this causes the dark-colored zones 334 to expand and light-colored zones 333 to contract. The expansion of zones 334 and the contraction of zones 333 are configured to be detected by the light-collecting array 332. A processor (not shown) is configured to collect and interpret data as partial and/or full occlusion, based on such detection. The present invention is also configured to interpret reduction of tube's size as leakage of fluid from the tube. Further, periodic change in tube's diameter can be interpreted as a normal pulsating fluid delivery. In some embodiments, the sensibility of the occlusion detection method above can be adjusted by changing the distance between the light-emitting source 331 and the light-collecting array 332.

FIG. 5A illustrates yet another preferred embodiment of an optical detection device for detecting pressure variation in the fluid delivery tube 510. The optical device includes a light-collecting array 542 and a light-emitting source 541. The array 542 and the source 541 are configured to be positioned on the same side of a dedicated region 520. In this embodiment, the light emitted by the light-emitting source 541 is configured to be reflected by the opposite side of the dedicated region 520 and then sensed by the light-collecting array 542.

FIGS. 5B and 5C illustrate downstream occlusion detection in the fluid delivery tube 510. In some embodiments, an upstream pressure elevation in the tube 510 is configured to induce a radial expansion of the dedicated region 520. A beam of light 543 emitted by the light-emitting source 541 is reflected at a particular angle. The angle of reflection is configured to vary in proportion to a curvature of the dedicated region 520. The beam 543 is consequently configured to be detected by the light collecting array 542. A processor (not shown) collects light beam 543 reflection data and is configured to interpret it as occlusion or any other tube condition, such as leakage. In some embodiments, reduction of tube's size can be interpreted as leakage. Additionally, periodic change in tube's diameter can also be interpreted as a normal pulsating fluid delivery.

FIG. 6 illustrates another embodiment of the present invention, in which radial expansion is sensed by a pressure sensor 609. A housing 608 surrounds at least a portion of a fluid delivery tube 610. The tube 610 is configured to be coupled to the pressure sensor 609. The pressure sensor 609 is configured to be positioned in close proximity to a wall 607 of the tube 610. The pressure sensor 609 can be configured to be electrically coupled to at least one resistor that may be arranged in a Wheatstone bridge (not shown in FIG. 6).

When a downstream occlusion occurs, an upstream pressure in the fluid delivery tube 610 causes radial expansion of the tube wall 607. The radial expansion of the tube wall 607 is configured to cause deformation of the pressure sensor 609 (an exemplary pressure sensor can be a Metrodyne Microsystems's MPS-1060 sensor, or any other sensor). This deformation further alters sensor's 609 resistance. A processor (not shown in FIG. 6) configured to be coupled to the system can interpret such change as occlusion.

Figure 7A:
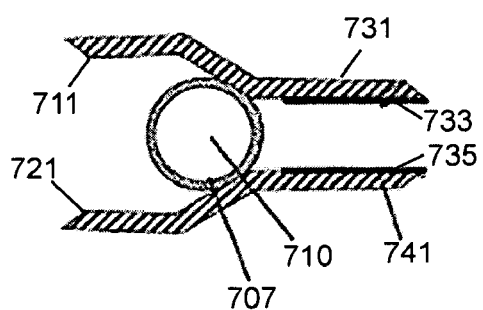
FIGS. 7A-7B illustrate an exemplary tube having a pressure sensor and two levers for detecting an occlusion using variant capacitance, according to the present invention.
Figure 7B:
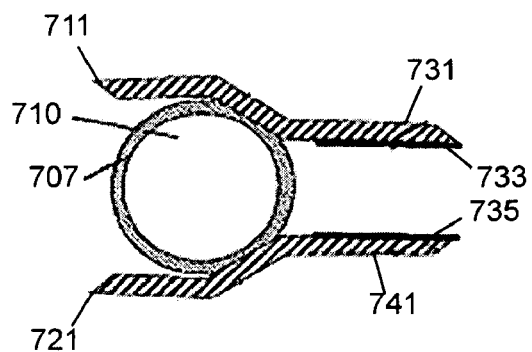

FIGS. 7A-B illustrate another embodiment of the present invention's system for monitoring pressure changes in the delivery tube 710 and fluid delivery tube's wall 707 expansion. The system includes two levers 711, 721 configured to embrace at least a portion of tube's wall 707. The levers 711, 721 further include tail portions 731, 741, respectively. The tail portions 731, 741 are configured to include electrically conductive regions 733, 735, respectively. In some embodiments, the electrically conductive regions 733, 735 are configured to be metallic plates. As such, the conductive regions 733, 735 are configured to form a capacitor. The capacitance of which is configured to change in accordance with the distance between the regions 733 and 735. Thus, when the fluid delivery tube 710 expands due to a downstream occlusion, it displaces levers 711, 721, which in turn affect the distance between the conductive regions 733, 735. Hence, the capacitance of the capacitor formed by the conductive regions 733 and 735 changes accordingly. In some embodiments, a processor (not shown in FIG. 7) configured to be coupled to the system is configured to interpret such change in capacitance. Based on the amount of the change, the processor can estimate the change in a diameter of the fluid delivery tube 710. The processor can further determine whether the change in the diameter is a result of a downstream occlusion in the fluid delivery tube 710, a leakage in the tube, or a normal pulsating delivery of a therapeutic fluid through the tube 710.

Figure 8A:
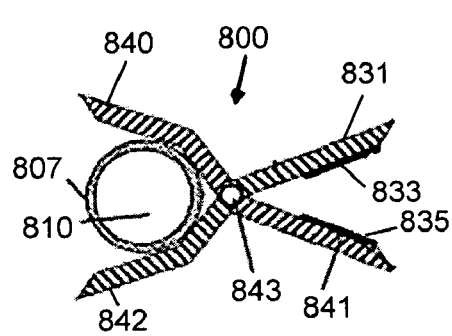
FIGS. 8A-8B illustrate an exemplary tube configured to be embraced by levers that are further configured to pivot around an axle for detecting an occlusion using variant capacitance, according to the present invention.
Figure 8B:
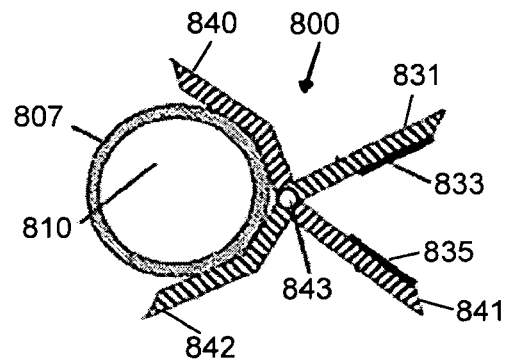

FIGS. 8A-8B illustrate another embodiment where a wall 807 of the fluid delivery tube 810 is configured to be embraced by levers 840, 842. The levers 840, 842 are configured to pivot around an axis 843. In the embodiment shown in FIG. 8, the levers 840, 842 are configured to have a scissors-like shape. As can be understood by one skilled in the art, other types of arrangement of levers 840, 842 are possible. Similarly to the embodiment illustrated in FIGS. 7A-7B, the levers 840, 842 are configured to include tail portions 831, 841. The tail portions 831, 841 are configured to include conductive regions 833, 835. Similarly to the embodiment of FIGS. 7A-7B, the conductive regions 833, 835 are configured to form a capacitor once current is passed through the regions 833, 835. Capacitance of this capacitor depends on the distance between the conductive regions 833, 835. As such, variation in the distance between regions 833, 835 causes variation of capacitance in the capacitor formed by the regions 833, 835. A processor (not shown in FIGS. 8A-8B) can be configured to be coupled to the system 800 and can be further configured to interpret variation in the distance between the regions 833, 835 as variation of pressure in tube 810. Thus, the processor can be configured to interpret change of pressure in the fluid delivery tube 810 as either downstream occlusion, leakage in the tube, normal pulsating delivery of the fluid, or any other condition in the tube.

FIGS. 9A-9B and 10A-10B illustrate longitudinal and cross sectional views of an exemplary fluid delivery tube 910, according to the present invention. In the illustrated embodiments, an L-shaped tubular protrusion 930 is configured to extend from the fluid delivery tube 910. The protrusion 930 further includes a first end 950 and a second end 960. First end 950 of the tubular protrusion 930 is configured to be closed (i.e., it is a blind end) and the second end 960 is configured to be open such that fluid communication is allowed between tube 910 and tubular protrusion 930. As can be understood by one skilled in the art, the tubular protrusion 930 can be configured to be a Bourdon gauge that can be further configured to change its configuration in response to pressure variation in fluid delivery tube 910. In some embodiments, such variation of tubular protrusion's configuration can be detected by various methods, e.g., optical detection methods, force and pressure sensing methods.

Figure 9A:
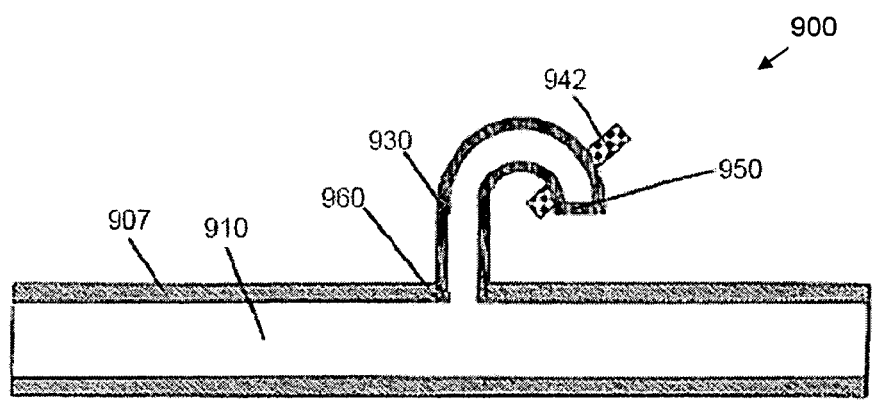
FIGS. 9A-9B are longitudinal cross-sectional views of an exemplary tube having an L-shaped tubular protrusion constituting a Burdon gauge and having a light-collecting array and a light-emitting source positioned on the opposite sides of the tubular protrusion, according to the present invention.
Figure 9B:
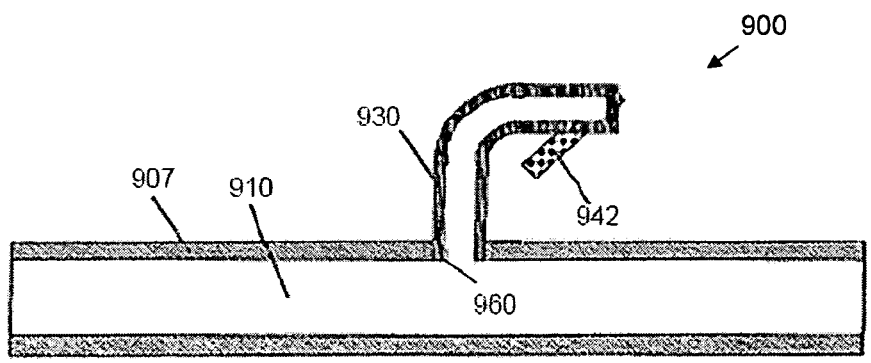
Figures 10A, 10B:
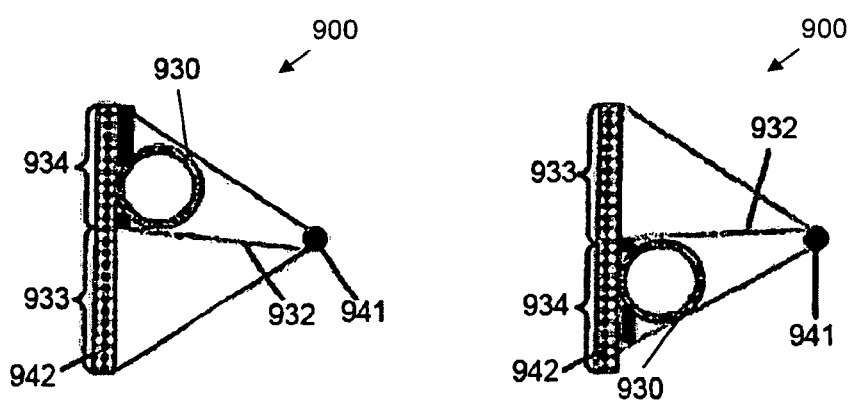
FIGS. 10A-10B are transversal cross-sectional views of an exemplary tube having an L-shaped tubular protrusion constituting a Burdon gauge and having a light-collecting array and a light-emitting source positioned on the opposite sides of the tubular protrusion, according to the present invention.

The fluid delivery tube 910 further includes a light-collecting array 942 (in some embodiments, the array can be a small CCD sensor) and a light-emitting source 941 (shown in FIGS. 10A-10B). The array 942 and the source 941 are configured to be located on the opposite sides of the protrusion 930 and specifically on the opposite sides of the closed end 950, as illustrated in FIGS. 9A-9B. Thus, the protrusion 930 is configured to block the light 932 emanating from the source 941 to the light-collecting array 942.

FIGS. 10A-10B are cross-sectional views of the fluid delivery tube 910 illustrated in FIGS. 9A-9B, respectively. As illustrated in FIGS. 10A-10B, the light collecting array 942 includes a shaded portion 934 and an illuminated portion 933. The shaded portion 934 represents a portion of the light collecting array 942 that is blocked by the protrusion 930 of the tube 910. The illuminated portion 933 represents a portion of the light collecting array 942 that is not currently blocked by the protrusion 930. Because of downstream occlusions (or any other conditions occurring in the tube), locations of the shaded portion 934 and the illuminated portion 933 on the light collecting array 942 may change, as shown in FIGS. 10A-10B. The location change is caused by the movement of the closed end 950. The movement of the closed end 950 is caused by rising pressure within the tube 910 (e.g., pressure rise caused by a Bourdon effect occlusion within the tube 910). FIG. 9A (and corresponding FIG. 10A) illustrates that there is substantially no pressure change within the tube 910 and, hence, no downstream occlusion has occurred in the tube 910. This is illustrated by the closed end 950 have a substantially curved shape, as illustrated in FIG. 9A. FIG. 9B (and corresponding FIG. 10B) illustrates that there is increase and/or other change in pressure within the tube 910 that may be caused by a downstream occlusion or any other effect. Such change in pressure causes the closed end 950 to become substantially straight, as illustrated in FIG. 9B. Thus, as the closed end 950 becomes substantially straight, its shadow (produced as a result of the light 932 emitted by the light source 941 towards light collecting array 942) shifts along the light collecting array 942, as illustrated in FIGS. 10A-10B. In some embodiments, a processor (not shown in FIGS. 9A-10B) can be configured to be coupled to the system 900 and interpret shifting of the shaded portions 934 as caused by a downstream occlusion, normal pulsating operation, leakage in the tube, or any other conditions.

Figure 11A:
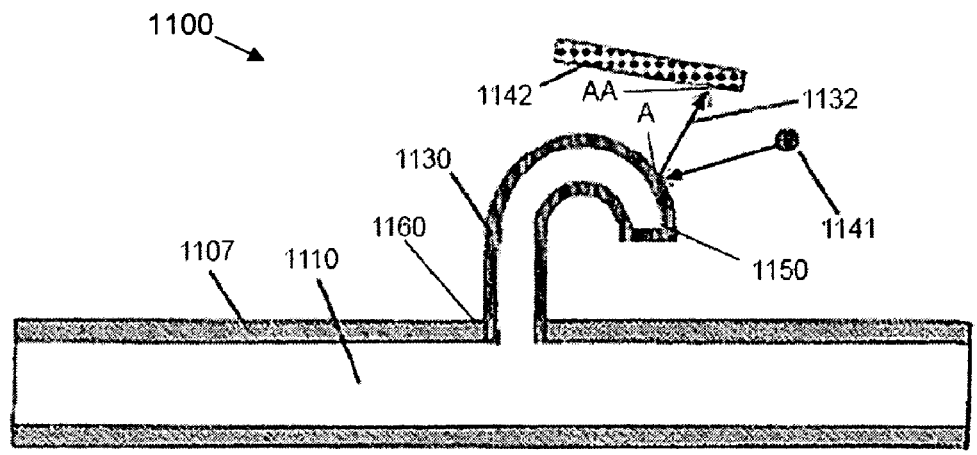
FIGS. 11A-11B are longitudinal cross-sectional views of an exemplary tube having an L-shaped tubular protrusion constituting a Burdon gauge and having a light-collecting array and a light-emitting source positioned on the same side of the tubular protrusion, according to the present invention.
Figure 11B:
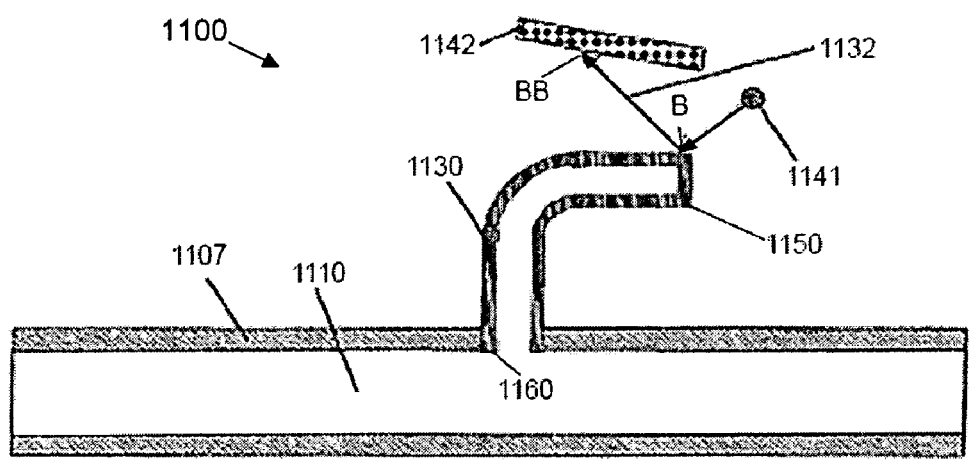

FIGS. 11A-11B are longitudinal views of another embodiment of the tube 1110. The tube 1110 includes protrusion 1130. Protrusion 1130 includes a closed end 1150 and an open end 1160. The open end 1160 communicates with the main tube 1110. In this embodiment, a light collecting array 1142 and a light-emitting source 1141 are located at the same side of the protrusion 1130 and, more specifically, on the same side of the closed end 1150. Similarly to FIGS. 9A-10B, light beam 1132, emitted by the source 1141, is reflected off of a surface of the closed end 1150 of the protrusion 1130. The reflected light beam 1132 is collected by the light collecting array 1142.

As the pressure in the tube 1110 changes, the closed end 1150 of the protrusion 1130 is configured to become straight (FIG. 11B) as opposed to substantially curved (FIG. 11A). Such change causes the angle and the location of reflection formed by the light beam 1132 on the surface of the closed end 1150 to change. As shown in FIG. 11A, light beam 1132 emitted by the source 1141 hits the closed end 1150 at location A and is collected at location AA on the light collecting array 1142. Once the closed end 1150 straightens, the light beam 1132 hits the closed end 1150 at location B and is collected at location BB on the light collecting array 1142, as illustrated in FIG. 11B. A processor (not shown in FIGS. 11A-11B) may be configured to be coupled to the system 1100 and interpret such change of collection location as downstream occlusion, normal pulsating delivery of fluid through the tube 1110, leakage in the tube 1110, or any other condition occurring in the system 1100 that causes change of location.

Figure 12:
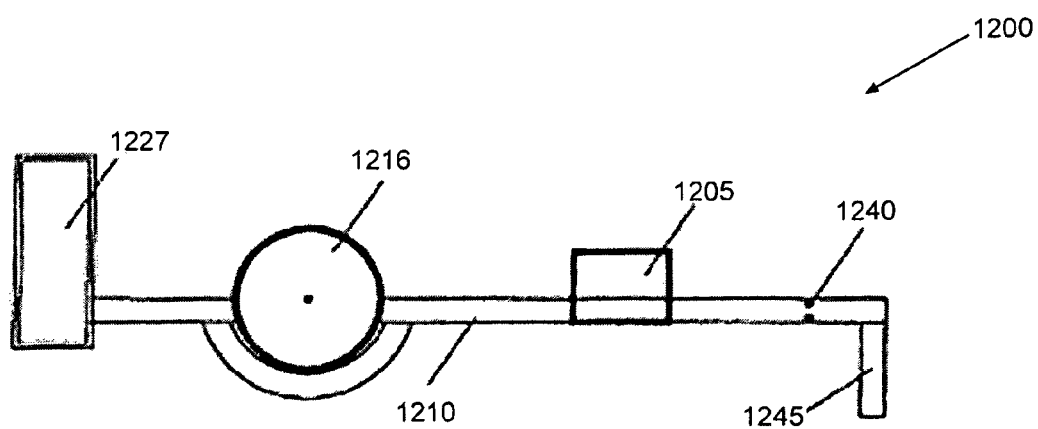
FIG. 12 illustrates an exemplary embodiment of a dispensing unit, according to the present invention.
Figure 13:
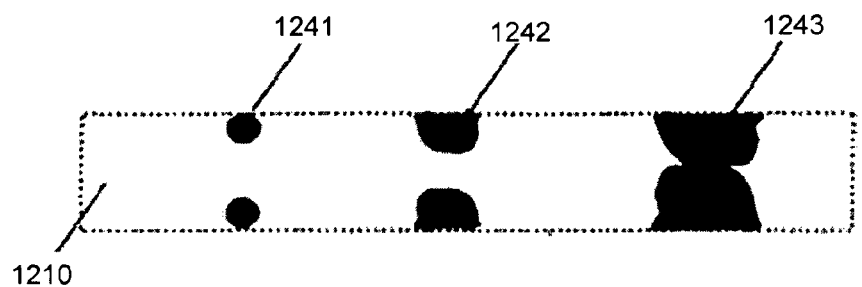
FIG. 13 illustrates an exemplary tube having partial and/or complete occlusions.

FIG. 12 illustrates an exemplary dispensing unit 1200, according to the present invention. The dispensing unit 1200 includes a reservoir 1227 that contains therapeutic fluid (e.g. insulin), a cannula 1245, a pump 1216, a delivery tube 1210, and an occlusion sensor 1205. The therapeutic fluid is configured to be delivered to the patient through the cannula 1245. As can be understood by one skilled in the art, the occlusion sensor 1205 can be a pressure sensor, a capacitance sensor, an optical sensor, or any other suitable sensor. The occlusion sensor 1205 is configured to detect an occlusion occurring in the tube 1210. As illustrated in FIG. 13, such an occlusion 1240 can be a partial occlusion 1241, 1242 (where occlusions 1241 and 1242 differ by a degree of actual occlusion in the tube 1210; in the shown example, occlusion 1242 is greater than occlusion 1241) or a complete occlusion 1243. As can be understood by one skilled in the art, the tube 1210 can have one or more occlusions 1240 occurring at the same time. In some embodiments, the therapeutic fluid can be delivered to the patient via a pulsating pumping mechanism. Waves generated by the pulsating mechanism in the fluid delivery tube 1210 can be depicted in pressure-time plots, as illustrated in FIGS. 14A-14C.

Figure 14A:
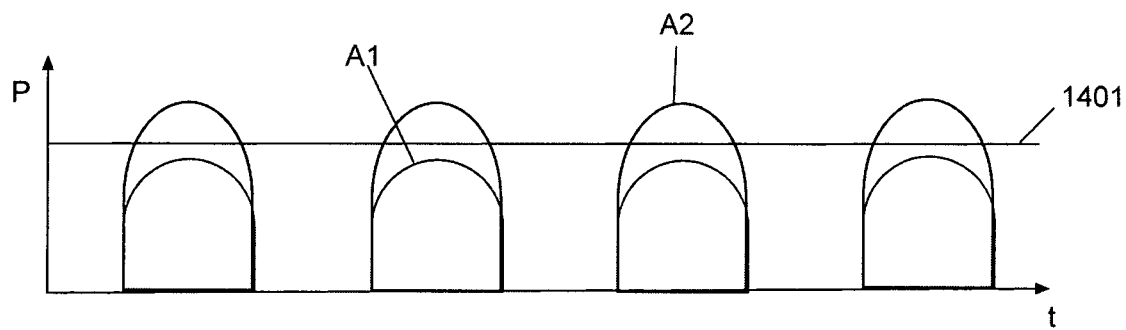
FIGS. 14A-14C illustrate exemplary pressure-time graphs representing fluid delivery tube's pressure, where the tube includes a pulsating pumping mechanism, according to the present invention.
Figure 14B:
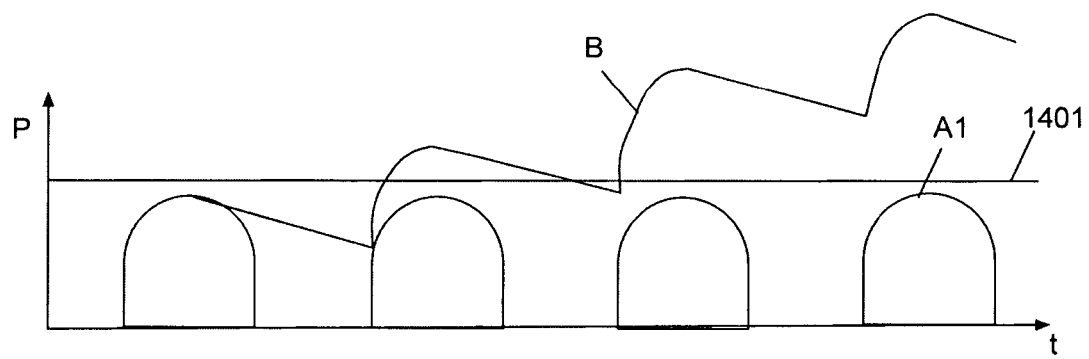
Figure 14C:
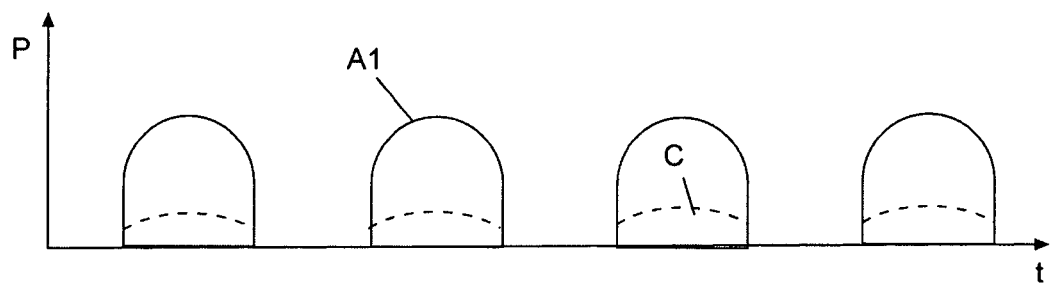

As shown in the FIGS. 14A-14C, y-axis of the plots corresponds to pressure exerted by the fluid in the fluid delivery tube and x-axis corresponds to time over which such pressure is exerted. Since therapeutic fluid is delivered by a pulsating mechanism, a substantially non-occluded delivery of the fluid to the patient can be represented by curve A1 having equally spaced peaks (corresponding to pulses generated by the pulsating mechanism) on the pressure-time plot. This is illustrated in FIGS. 14A-14C. In some embodiments, a threshold pressure setting may be set by the system that indicates above which pressure occlusion in the tube 1210 begins to occur. This is illustrated by a line 1401 in FIGS. 14A and 14B. As can be understood by one skilled in the art, threshold setting can be adjusted according to the desired setting of the system. During a substantially non-occluded delivery of the therapeutic fluid, the heights of all of the equally spaced peaks are configured to be below the threshold line 1401, as illustrated on the plot in FIG. 14A. Mild occlusion (e.g., 40% of the tube is occluded) is normal during operation of the system 1200. Periods of mild occlusion are illustrated by a curve A2 in FIG. 14A. The peaks' heights of the curve A2 are slightly higher than the threshold line 1401. In some embodiments, the system 1200 may choose to ignore detection of a mild occlusion by the sensor 1205. Yet, in other alternate embodiments, the sensor 1205 may be configured to various degrees of occlusions and the system 1200 can be configured to act as desired.

FIG. 14b is another pressure-time plot illustrating a substantially non-occluded delivery of fluid (represented by curve A1) and delivery of fluid during periods of partial occlusions 1241, 1242 and full occlusions 1243 of the tube 1210 (FIG. 13). Periods of partial and/or full occlusions of the delivery tube are illustrated by curve B. Because tube 1210 is experiencing an occlusion (whether partial or full), fluid delivery through tube 1210 becomes sporadic. As such, this causes fluid built-up, which corresponds to an increase in fluid pressure inside the tube 1210. Thus, the pressure-time curve representing fluid delivery through the tube loses its periodicity and symmetry, as illustrated in FIG. 14B. Because of rise in amplitude of the pressure, curve B crosses threshold line 1401 indicating an occlusion condition within tube 1210. The occlusion sensor 1205 is configured to detect these changing patterns of curve B and supply signals indicative of the occlusion in the tube 1210 to a processor (not shown in FIG. 12). The processor (and/or other electronic components) can be configured to process and interpret these signals and generate a warning and/or an alarm to the patient.

In some embodiments, the system 1200 can be configured to detect low-flow conditions within the delivery tube 1210. Low-flow conditions may occur when the pulsating flow through the tube 1210 is lower than is set by the system. In some embodiments, the low-flow conditions may occur when there is a leak in the tube 1210. FIG. 14C is a pressure-time plot illustrating monitoring of flow conditions within the tube 1210. FIG. 14C illustrates curve A1 that corresponds to substantially non-occluded delivery of the fluid and curve C that corresponds to a low-flow condition. As can be seen from FIG. 14C, peaks in curve C have a significantly lower height than peaks in curve A1, which is indicative of a low flow condition in the tube 1210.

Figure 15:
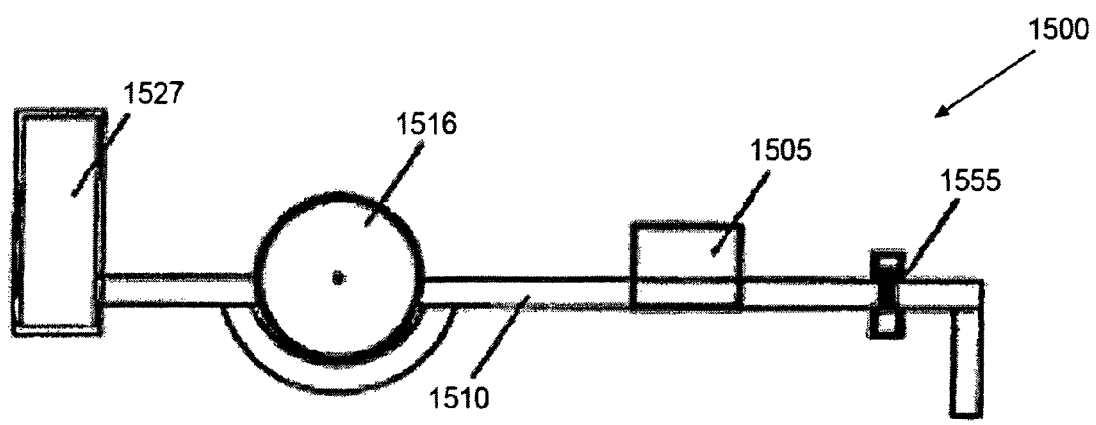
FIG. 15 illustrates an exemplary tube having a valve and an occlusion detector, according to the present invention.

FIG. 15 illustrates another exemplary fluid delivery system 1500, according to the present invention. Similar to the fluid delivery system shown in FIG. 12, the fluid delivery system 1500 includes a reservoir 1527, a pump 1516, a fluid delivery tube 1510 and an occlusion sensor 1505. Additionally, the fluid delivery system 1500 also includes a control valve 1555. The control valve 1555 has a closed and an open state. In the closed state, the valve 1555 does not allow any fluid to be delivered through the tube 1510. In the open state, the valve 1555 allows fluid delivery through the tube 1510. In some embodiments of the present invention, a processor (not shown in FIG. 15) can be configured to be coupled to the valve 1555 and to control opening and closing of the valve 1555 based on operation of the pump 1516.

FIG. 16A is a pressure-time plot illustrating operation of the pump 1516 shown in FIG. 15. In some embodiments, the valve 1555 operation can be configured to be synchronized with a normal operation of the pump 1516. This is illustrated by the curve A in FIG. 16A. The "normal" operation of the pump 1516 is characterized by a substantially non-occluded delivery of the fluid through the tube 1510. As illustrated in FIG. 16A, curve A includes periods of pressure alteration when pressure inside the tube begins to rise during pumping operating of the pump 1516. During this time, the valve 1555 remains closed. This is illustrated by segments 1625 (a, b, c). When pumping operation halts and the valve 1555 remains closed, the pressure reaches an upper limit, i.e., a plateau 1627 (a, b, c). As soon as the valve 1555 is opened, i.e., occurring at the end of plateaus 1627, the pressure inside the tube 1510 begins to drop. This is illustrated by the segments 1629 (a, b, c). During "normal" operation of the pump, curve A is periodic in nature and the amplitude of each period is substantially the same throughout the curve.

FIG. 16B is a pressure-time plot illustrating operation of the pump 1516 during total or partial occlusion occurring within the tube 1510. FIG. 16B includes a curve B, representing operation of the pump 1516 during total occlusion (FIG. 13), and a curve C representing operation of the pump 1516 during partial occlusion (FIG. 13). Similar to the discussion of FIGS. 14A-14C, curves B and C do not have the same periodicity or substantially the same amplitude, as curve A shown in FIG. 16A. The severity of change in periodicity and amplitude is dependent on the severity of occlusion occurring within the tube 1510. As the occlusion in the tube 1510 increases, the periodicity of the curve decreases and the amplitude increases (as shown by curve B, representing total occlusion).

FIG. 16C is a pressure-time plot illustrating operation of the pump 1516 when air is present in the tube 1510 and a very mild occlusion occurs. FIG. 16C includes a curve E, representing operation of the pump 1516 when a large amount of air is present in the tube 1510, and a curve D, representing operation of the pump 1516 when a small amount of air is present in the tube 1510. As shown in FIG. 16C, when air is present in the tube 1510, the pressure inside the tube decreases, which is illustrated by the decreasing amplitude. In some embodiments, valve 1555 can be configured to provide high sensitivity required for occlusion detection sensors even when there is a fluid leak or air is present in the tube 1510. The valve 1555 can be configured to enhance signals corresponding to variation in pressure within the tube 1510. This improves sensitivity of occlusion detection and allows detection of variety of flow conditions, including partial or full occlusion or lack of fluid in the reservoir/leakage.

In some embodiments of the present invention, the fluid delivery device discussed above with regard to FIGS. 1-16C is configured to be attached to the patient. As explained above, the device can be configured to be a patch unit adherable to the skin of the patient. The fluid delivery device is configured to pump therapeutic fluid to the patient using a dispensing unit having a pumping mechanism. The dispensing unit is controlled by a remote control unit. The dispensing unit is configured to communicate with the remote control unit. The dispensing unit includes a delivery tube having an inlet portion and an outlet portion, where the inlet portion is configured to be coupled to a reservoir containing therapeutic fluid, as discussed above with regard to FIGS. 1-16C. The dispensing unit also includes a peristaltic pump having a stator plate and rotary wheel with rollers, wherein the stator plate and the rollers are configured to squeeze the fluid delivery tube. In some embodiments, the peristaltic pump can be configured to pump fluid from the reservoir via the inlet portion of the tube to the outlet portion upon squeezing the fluid delivery tube. The dispensing unit also includes an occlusion sensor that can be configured to be located near the outlet portion of the fluid delivery tube, as discussed above with regard to FIGS. 1-16C. The sensor can be configured to detect occlusion within the fluid delivery tube.

Example embodiments of the methods and components of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments, but should be defined only in accordance with the following claims and their equivalents.

What is claimed is:

1. A fluid delivery device for delivering therapeutic fluid to a patient comprising:
   a disposable part comprising a fluid delivery tube, said fluid delivery tube is substantially accommodated within a housing of said disposable part;
   a reusable part comprising at least a first portion of an occlusion detection sensor configured to detect occlusion within a fluid passageway including at least said fluid delivery tube;
   wherein:
      said fluid delivery tube includes a protrusion extending from said fluid delivery tube, said protrusion is configured to change its orientation with respect to said fluid delivery tube when fluid pressure within said fluid delivery tube increases;
      said occlusion detection sensor is configured to detect said change in the orientation of said protrusion; and
      said occlusion detection sensor is operative upon coupling said reusable part and said disposable part.

2. The fluid delivery device according to claim 1, wherein:
   the disposable part further comprises a reservoir coupled to said fluid delivery tube, from which therapeutic fluid is delivered to the patient via said fluid delivery tube; and
   the reusable part further comprises at least a portion of a pump for pumping the therapeutic fluid from said reservoir.

3. The fluid delivery device according to claim 2, wherein said pump comprises a peristaltic pump which includes:
   a stator plate located in the disposable part; and
   a rotary wheel with rollers located in the reusable part, wherein:
      said stator plate and said rollers are configured to squeeze said fluid delivery tube upon coupling the reusable part to the disposable part; and
      said peristaltic pump is configured to pump fluid from said reservoir via an inlet portion of said fluid delivery tube to an outlet portion of said fluid delivery tube upon squeezing said fluid delivery tube.

4. The fluid delivery device according to claim 1, wherein said occlusion detection sensor is configured to detect states of occlusion within said fluid passageway selected from a group consisting of: no occlusion, partial occlusion, and total occlusion.

5. The fluid delivery device according to claim 1, further comprising an alarm configured to alert the patient when said occlusion detection sensor detects at least partial occlusion within said fluid passageway.

6. The fluid delivery device according to claim 1, wherein said occlusion detection sensor is further configured to detect normal delivery of therapeutic fluid to the patient based on a predetermined pressure value of the fluid within said fluid delivery tube, the predetermined pressure value being associated with said normal delivery.

7. The fluid delivery device according to claim 6, wherein said normal delivery is a pulsating delivery.

8. The fluid delivery device according to claim 1, wherein said occlusion detection sensor is further configured to detect leakage of therapeutic fluid from said fluid passageway based on a pressure of the fluid within said fluid delivery tube dropping below a threshold pressure value.

9. The fluid delivery device according to claim 1, wherein said occlusion detection sensor is further configured to detect presence of air within said fluid passageway.

10. The fluid delivery device according to claim 1, further comprising a control valve, wherein said control valve is configured to control delivery of the therapeutic fluid in said fluid delivery tube for variation of fluid pressure within said fluid delivery tube.

11. The fluid delivery device according to claim 10, wherein said control valve is configured such that when said control valve is closed, the fluid pressure within said fluid delivery tube increases, and when said control valve is open, the fluid pressure within said fluid delivery tube decreases.

12. The fluid delivery device according to claim 11, wherein during a normal operation of the fluid delivery device, the increase and decrease of said fluid pressure within said fluid delivery tube are periodic.

13. The fluid delivery device according to claim 1, wherein said reusable part further includes electronic components configured to at least one of collect data, process data and perform data analysis.

14. The fluid delivery device according to claim 1, wherein:
   said disposable part further comprises at least a second portion of said occlusion detection sensor, and said first portion of said occlusion detection sensor is operatively coupled to said second portion of said occlusion detection sensor upon coupling said reusable part and said disposable part.

15. A fluid delivery device for delivering therapeutic fluid to a patient comprising:
a disposable part comprising a fluid delivery tube, said fluid delivery tube is substantially accommodated within a housing of said disposable part; and
a reusable part comprising at least a first portion of an occlusion detection sensor configured to detect occlusion within a fluid passageway including at least said fluid delivery tube,
wherein:
said fluid delivery tube includes an occlusion detection portion,
said occlusion detection sensor comprises a light emitting source configured to emit light toward said occlusion detection portion, and a light collecting array configured to collect said light, wherein said occlusion detection portion is configured to reflect said light toward said light collecting array at a reflection angle,
said occlusion detection sensor is configured to detect occlusion within said fluid passageway based on a change in said reflection angle, said change corresponding to an alteration of a property of said occlusion detection portion when at least one condition occurs within said fluid delivery tube, and
said occlusion detection sensor is operative upon coupling said reusable part and said disposable part.

16. The fluid delivery device according to claim 15, wherein said at least one condition is a change in fluid pressure within said fluid delivery tube.

17. The fluid delivery device according to claim 16, wherein said occlusion detection portion is configured to expand when said fluid pressure within said fluid delivery tube increases.

18. The fluid delivery device according to claim 15, wherein:
the disposable part further comprises a reservoir coupled to said fluid delivery tube, from which therapeutic fluid is delivered to the patient via said fluid delivery tube, and
the reusable part further comprises at least a portion of a pump for pumping the therapeutic fluid from said reservoir.

19. The fluid delivery device according to claim 15, further comprising an alarm configured to alert the patient when said occlusion detection sensor detects at least partial occlusion within said fluid passageway.

20. The fluid delivery device according to claim 15, wherein said reusable part further includes electronic components configured to at least one of collect data, process data and perform data analysis.

21. The fluid delivery device according to claim 15, wherein said property of said occlusion detection portion is selected from a group consisting of: shape, size, diameter, dimension, configuration, and orientation of said occlusion detection portion.

22. The fluid delivery device according to claim 15, wherein:
said disposable part further comprises at least a second portion of said occlusion detection sensor, and
said first portion of said occlusion detection sensor is operatively coupled to said second portion of said occlusion detection sensor upon coupling said reusable part and said disposable part.

23. A fluid delivery device for delivering therapeutic fluid to a patient comprising:
a disposable part comprising a fluid delivery tube, said fluid delivery tube being substantially accommodated within a housing of said disposable part; and
a reusable part comprising at least a first portion of an occlusion detection sensor configured to detect occlusion within a fluid passageway including at least said fluid delivery tube;
wherein:
said fluid delivery tube includes an occlusion detection portion;
said occlusion detection sensor comprises a light emitting source configured to emit light toward said occlusion detection portion, and a light collecting array configured to collect said light, wherein said occlusion detection portion is configured to block at least a portion of said light;
said occlusion detection sensor is configured to detect occlusion within said fluid passageway based on at least one of an amount of light collected by said light collecting array and an amount of light blocked by said occlusion detection portion, wherein said at least one of the amount of light collected by said light collecting array and the amount of light blocked by said occlusion detection portion corresponds to an alteration of a property of said occlusion detection portion when at least one condition occurs within said fluid delivery tube; and
said occlusion detection sensor is operative upon coupling said reusable part and said disposable part.

24. The fluid delivery device according to claim 23, wherein said at least one condition comprises a change in fluid pressure within said fluid delivery tube.

25. The fluid delivery device according to claim 24, wherein said occlusion detection portion is configured to expand when said fluid pressure within said fluid delivery tube increases.

26. The fluid delivery device according to claim 23, wherein:
the disposable part further comprises a reservoir coupled to said fluid delivery tube, from which therapeutic fluid is delivered to the patient via said fluid delivery tube, and
the reusable part further comprises at least a portion of a pump for pumping the therapeutic fluid from said reservoir.

27. The fluid delivery device according to claim 23, further comprising an alarm configured to alert the patient when said occlusion detection sensor detects at least partial occlusion within said fluid passageway.

28. The fluid delivery device according to claim 23, wherein said reusable part further includes electronic components configured to at least one of collect data, process data and perform data analysis.

29. The fluid delivery device according to claim 23, wherein said property of said occlusion detection portion is selected from a group consisting of: shape, size, diameter, dimension, configuration, and orientation of said occlusion detection portion.

30. The fluid delivery device according to claim 23, wherein:
said disposable part further comprises at least a second portion of said occlusion detection sensor, and
said first portion of said occlusion detection sensor is operatively coupled to said second portion of said occlusion detection sensor upon coupling said reusable part and said disposable part.

31. A fluid delivery device for delivering therapeutic fluid to a patient comprising:
- a disposable part comprising a fluid delivery tube, said fluid delivery tube is substantially accommodated within a housing of said disposable part;
- a reusable part comprising at least a first portion of an occlusion detection sensor configured to detect occlusion within a fluid passageway including at least said fluid delivery tube;

wherein:
said fluid delivery tube includes an occlusion detection portion;
said occlusion detection sensor comprises a light emitting source configured to emit light and a light collecting array configured to collect said light, wherein said light emitting source and said light collecting array are configured to be located on the same side of said occlusion detection portion;
said occlusion detection sensor is configured to detect alteration of a property of said occlusion detection portion when at least one condition occurs within said fluid delivery tube; and
said occlusion detection sensor is operative upon coupling said reusable part and said disposable part.

32. The fluid delivery device according to claim 31, wherein said at least one condition comprises a change in fluid pressure within said fluid delivery tube.

33. The fluid delivery device according to claim 32, wherein said occlusion detection portion is configured to expand when said fluid pressure within said fluid delivery tube increases.

34. The fluid delivery device according to claim 31, wherein:
the disposable part further comprises a reservoir coupled to said fluid delivery tube, from which therapeutic fluid is delivered to the patient via said fluid delivery tube; and
the reusable part further comprises at least a portion of a pump for pumping the therapeutic fluid from said reservoir.

35. The fluid delivery device according to claim 34, wherein said pump comprises a peristaltic pump, said peristaltic pump including:
a stator plate located in the disposable part; and
a rotary wheel with rollers located in the reusable part, wherein
said stator plate and said rollers are configured to squeeze said fluid delivery tube upon coupling the reusable part to the disposable part; and
said peristaltic pump is configured to pump fluid from said reservoir via an inlet portion of said fluid delivery tube to an outlet portion of said fluid delivery tube upon squeezing said fluid delivery tube.

36. The fluid delivery device according to claim 31, wherein said occlusion detection sensor is further configured to detect normal delivery of therapeutic fluid to the patient based on a predetermined pressure value of the fluid within said fluid delivery tube, the predetermined pressure value being associated with said normal delivery.

37. The fluid delivery device according to claim 31, wherein said normal delivery is a pulsating delivery.

38. The fluid delivery device according to claim 31, wherein said occlusion detection sensor is further configured to detect leakage of therapeutic fluid from said fluid passageway based on a pressure of the fluid within said fluid delivery tube dropping below a threshold pressure value.

39. The fluid delivery device according to claim 31, wherein said occlusion detection sensor is further configured to detect presence of air within said fluid passageway.

40. The fluid delivery device according to claim 31, further comprising a control valve, wherein said control valve is configured to control delivery of the therapeutic fluid in said fluid delivery tube for variation of fluid pressure within said fluid delivery tube.

41. The fluid delivery device according to claim 31, further comprising an alarm configured to alert the patient when said occlusion detection sensor detects at least partial occlusion within said fluid passageway.

42. The fluid delivery device according to claim 31, wherein said reusable part further includes electronic components configured to at least one of collect data, process data and perform data analysis.

43. The fluid delivery device according to claim 31, wherein said property of said occlusion detection portion is selected from a group consisting of: shape, size, diameter, dimension, configuration, and orientation of said occlusion detection portion.

44. The fluid delivery device according to claim 31, wherein:
said disposable part further comprises at least a second portion of said occlusion detection sensor, and
said first portion of said occlusion detection sensor is operatively coupled to said second portion of said occlusion detection sensor upon coupling said reusable part and said disposable part.

45. A fluid delivery device for delivering therapeutic fluid to a patient comprising:
- a disposable part comprising a fluid delivery tube, said fluid delivery tube is substantially accommodated within a housing of said disposable part;
- a reusable part comprising at least a first portion of an occlusion detection sensor configured to detect occlusion within a fluid passageway including at least said fluid delivery tube;

wherein:
said fluid delivery tube includes an occlusion detection portion;
said occlusion detection sensor comprises a light emitting source configured to emit light and a light collecting array configured to collect said light, wherein said light emitting source and said light collecting array are configured to be located on opposite sides of said occlusion detection portion;
said occlusion detection sensor is configured to detect alteration of a property of said occlusion detection portion when at least one condition occurs within said fluid delivery tube; and
said occlusion detection sensor is operative upon coupling said reusable part and said disposable part.

46. The fluid delivery device according to claim 45, wherein said at least one condition is a change in fluid pressure within said fluid delivery tube.

47. The fluid delivery device according to claim 46, wherein said occlusion detection portion is configured to expand when said fluid pressure within said fluid delivery tube increases.

48. The fluid delivery device according to claim 45, wherein:
the disposable part further comprises a reservoir coupled to said fluid delivery tube, from which therapeutic fluid is delivered to the patient via said fluid delivery tube; and the reusable part further comprises at least a portion of a pump for pumping the therapeutic fluid from said reservoir.

49. The fluid delivery device according to claim 48, wherein said pump comprises a peristaltic pump, said peristaltic pump including:
a stator plate located in the disposable part; and
a rotary wheel with rollers located in the reusable part,
wherein:
said stator plate and said rollers are configured to squeeze said fluid delivery tube upon coupling the reusable part to the disposable part, and
said peristaltic pump is configured to pump fluid from said reservoir via an inlet portion of said fluid delivery tube to an outlet portion of said fluid delivery tube upon squeezing said fluid delivery tube.

50. The fluid delivery device according to claim 45, wherein said occlusion detection sensor is further configured to detect normal delivery of therapeutic fluid to the patient based on a predetermined pressure value of the fluid within said fluid delivery tube, the predetermined pressure value being associated with said normal delivery.

51. The fluid delivery device according to claim 45, wherein said normal delivery is a pulsating delivery.

52. The fluid delivery device according to claim 45, wherein said occlusion detection sensor is further configured to detect leakage of therapeutic fluid from said fluid passageway based on a pressure of the fluid within said fluid delivery tube dropping below a threshold pressure value.

53. The fluid delivery device according to claim 45, wherein said occlusion detection sensor is further configured to detect presence of air within said fluid passageway.

54. The fluid delivery device according to claim 45, further comprising a control valve, wherein said control valve is configured to control delivery of the therapeutic fluid in said fluid delivery tube for variation of fluid pressure within said fluid delivery tube.

55. The fluid delivery device according to claim 45, further comprising an alarm configured to alert the patient when said occlusion detection sensor detects at least partial occlusion within said fluid passageway.

56. The fluid delivery device according to claim 45, wherein said reusable part further includes electronic components configured to at least one of collect data, process data and perform data analysis.

57. The fluid delivery device according to claim 45, wherein said property of said occlusion detection portion is selected from a group consisting of: shape, size, diameter, dimension, configuration, and orientation of said occlusion detection portion.

58. The fluid delivery device according to claim 45, wherein:
said disposable part further comprises at least a second portion of said occlusion detection sensor, and
said first portion of said occlusion detection sensor is operatively coupled to said second portion of said occlusion detection sensor upon coupling said reusable part and said disposable part.

59. A fluid delivery device for delivering therapeutic fluid to a patient comprising:
a disposable part comprising a fluid delivery tube, said fluid delivery tube is substantially accommodated within a housing of said disposable part; and
a reusable part comprising at least a first portion of an occlusion detection sensor configured to detect occlusion within a fluid passageway including at least said fluid delivery tube;

wherein:
said fluid delivery tube includes an occlusion detection portion;
said occlusion detection sensor comprises movable capacitance plates;
said occlusion detection portion is configured to change a distance between said movable capacitance plates upon change of fluid pressure within said fluid delivery tube;
said occlusion detection sensor is configured to detect occlusion within said fluid passageway based on a change in said distance between said movable capacitance plates, said change in said distance corresponding to an alteration of a property of said occlusion detection portion when said change in fluid pressure within said fluid delivery tube occurs; and
said occlusion detection sensor is operative upon coupling said reusable part and said disposable part.

60. The fluid delivery device according to claim 59, wherein said occlusion detection portion is configured to expand when said fluid pressure within said fluid delivery tube increases.

61. The fluid delivery device according to claim 59, wherein:
the disposable part further comprises a reservoir coupled to said fluid delivery tube, from which therapeutic fluid is delivered to the patient via said fluid delivery tube; and
the reusable part further comprises at least a portion of a pump for pumping the therapeutic fluid from said reservoir.

62. The fluid delivery device according to claim 60, wherein said pump comprises a peristaltic pump, said peristaltic pump including:
a stator plate located in the disposable part; and
a rotary wheel with rollers located in the reusable part,
wherein
said stator plate and said rollers are configured to squeeze said fluid delivery tube upon coupling the reusable part to the disposable part, and
said peristaltic pump is configured to pump fluid from said reservoir via an inlet portion of said fluid delivery tube to an outlet portion of said fluid delivery tube upon squeezing said fluid delivery tube.

63. The fluid delivery device according to claim 59, wherein said occlusion detection sensor is further configured to detect normal delivery of therapeutic fluid to the patient based on a predetermined pressure value of the fluid within said fluid delivery tube, the predetermined pressure value being associated with said normal delivery.

64. The fluid delivery device according to claim 59, wherein said normal delivery is a pulsating delivery.

65. The fluid delivery device according to claim 59, wherein said occlusion detection sensor is further configured to detect leakage of therapeutic fluid from said fluid passageway based on a pressure of the fluid within said fluid delivery tube dropping below a threshold pressure value.

66. The fluid delivery device according to claim 59, further comprising a control valve, wherein said control valve is configured to control delivery of the therapeutic fluid in said fluid delivery tube for variation of fluid pressure within said fluid delivery tube.

67. The fluid delivery device according to claim 59, further comprising an alarm device configured to alert the patient when said occlusion detection sensor detects at least partial occlusion within said fluid passageway.

68. The fluid delivery device according to claim 59, wherein said reusable part further includes electronic components configured to at least one of collect data, process data and perform data analysis.

69. The fluid delivery device according to claim 59, wherein said property of said occlusion detection portion is selected from a group consisting of: shape, size, diameter, dimension, configuration, orientation and other property of said occlusion detection portion.

70. The fluid delivery device according to claim 59, wherein said occlusion detection sensor is configured to be coupled to said occlusion detection portion of said fluid delivery tube.

71. The fluid delivery device according to claim 59, wherein:
- said disposable part further comprises at least a second portion of said occlusion detection sensor, and
- said first portion of said occlusion detection sensor is operatively coupled to said second portion of said occlusion detection sensor upon coupling said reusable part and said disposable part.

* * * * *